United States Patent [19]

Kennedy et al.

[11] 4,148,834

[45] Apr. 10, 1979

[54] PREPARATION OF SYNTHETIC HYDROCARBON LUBRICANTS

[75] Inventors: Carl D. Kennedy, Spartanburg, S.C.; Gene E. Nicks, Ponca City, Okla.

[73] Assignee: Continental Oil Company, Ponca City, Okla.

[21] Appl. No.: 884,679

[22] Filed: Mar. 8, 1978

Related U.S. Application Data

[63] Continuation of Ser. No. 566,549, Apr. 9, 1975, abandoned, which is a continuation-in-part of Ser. No. 453,601, Mar. 21, 1974, abandoned.

[51] Int. Cl.$^2$ .............................................. C07C 3/52
[52] U.S. Cl. .................. 260/671 B; 252/59; 260/671 G
[58] Field of Search ...................... 260/671 B, 671 G

[56] References Cited

U.S. PATENT DOCUMENTS

| 2,467,130 | 4/1949 | Hunt et al. | 260/671 |
| 2,479,120 | 8/1949 | Johnstone | 260/671 |
| 2,525,778 | 10/1950 | de Benneville et al. | 260/671 |
| 2,626,967 | 1/1953 | Darragh et al. | 260/671 |
| 2,871,254 | 1/1959 | Hoog et al. | 260/671 |
| 3,173,965 | 3/1965 | Pappas et al. | 260/671 |

Primary Examiner—C. Davis
Attorney, Agent, or Firm—Bayless E. Rutherford, Jr.

[57] ABSTRACT

This disclosure concerns an improved process for preparing a synthetic hydrocarbon lubricant composition, said composition consisting essentially of di-long-chain alkyl-substituted aromatic hydrocarbons. The improved process is directed to a two-step alkylation process, using linear mono-olefins as the alkylating agent, and in which the first alkylation is conducted using HF as the catalyst, wherein the improvement comprises using aluminum chloride or aluminum bromide as the catalyst for the second alkylation step. Use of aluminum chloride or aluminum bromide, instead of HF, in the second alkylation step results in a product having better low temperature properties.

10 Claims, No Drawings

PREPARATION OF SYNTHETIC HYDROCARBON LUBRICANTS

CROSS-REFERENCE TO RELATED APPLICATIONS

This application is a continuation of application Ser. No. 566,549, filed Apr. 9, 1975, now abandoned, which is a continuation-in-part of application Ser. No. 453,601, filed Mar. 21, 1974, now abandoned.

BACKGROUND AND FIELD OF THE INVENTION

1. Field of the Invention

The invention is in the field of synthetic hydrocarbon lubricants and the preparation thereof. Particularly it is in the field of preparing di-long-chain alkyl-substituted aromatic hydrocarbons by a two-step alkylation process.

BACKGROUND

The use of dialkylbenzenes, wherein the alkyl groups are linear and contain from 6 to 18, preferably 11 to 14, carbon atoms, as synthetic lubricants has been known for several years. One of the earliest disclosures of this nature is found in U.S. Pat. No. 3,173,965, 3,173,260 3,173,667 to Pappas and Kant. It is also known that compositions containing a major amount of di-long-chain alkyl-substituted aromatic hydrocarbons, wherein the aromatic moiety is phenyl, tolyl, or xylyl, are useful as low temperature lubricants. In general the synthetic hydrocarbon lubricants have a combination of physical properties, particularly pour point, viscosity index, and low temperature viscosity, which render them useful as low temperature lubricants.

2. Piror Art

The most pertinent prior are is believed to be U.S. Pat. No. 3,173,965. This patent teaches that dialkylbenzenes, suitable for use as lubricants, can be prepared by either a one- or two-step alkylation of benzene. Suitable alkylating agents include α-olefins. Suitable catalysts are $AlCl_3$, $AlBr_3$, $FeCl_3$, $SnCl_4$, $BF_3$, HF, $H_2SO_4$, $P_2O_5$, and $H_3PO_4$. The patent contains no recognition of the following: When the first alkylation step is conducted using HF as the catalyst, use of $AlCl_3$ or $AlBr_3$ as the catalyst in the second step results in a product having improved physical properties, particularly low temperature viscosity properties.

BRIEF DESCRIPTION OF THE INVENTION

Broadly stated, the present invention is directed to an improved process for preparing a synthetic hydrocarbon lubricant composition, consisting essentially of di-long-chain alkyl-substituted aromatic hydrocarbons. The improved process is a two-step alkylation process wherein an aromatic hydrocarbon is alkylated with a linear mono-olefin and in which hydrogen fluoride is used as the catalyst in the first alkylation step, wherein the improvement comprises using aluminum chloride or aluminum bromide as the catalyst for the second alkylation step.

More particularly, the present invention is directed to an improvement in the process fo preparing di-$C_6$-$C_{18}$ alkylbenzenes, wherein the alkyl groups are substantially linear, by a two-step alkylation process, using a linear mono-olefin as the alkylating agent, and in which hydrogen fluoride is used as the catalyst for the first alkylation step, the improvement comprising using as the catalyst for the second alkylation step aluminum chloride or aluminum bromide.

The improved process results in better low temperature viscosity properties for the product, which is particularly useful as a low temperature lubricant.

DETAILED DESCRIPTION

Materials Used

Suitable aromatic hydrocarbons for use in our process include benzene, toluene, xylene, and ethylbenzene. Benzene is the preferred aromatic hydrocarbon.

Suitable linear mono-olefins for use in our process contain from about 6 to about 18 carbon atoms, preferably from about 10 to about 14 carbon atoms. Either pure materials or mixtures of materials containing the designated number of carbon atoms can be used. The olefins are predominantly linear material but can contain minor amounts (e.g., 2 to about 15 weight percent) of branched chain olefins. The branched chain olefins appear to deteriorate the physical properties of the product. In addition, it should be mentioned that the olefin alkylating agent can contain paraffins of the same approximate molecular weight, which can be separated from the alkylation product by distillation.

The feedstock used in the second alkylation step, which is our invention, has the following typical composition:

|  | Weight % |
|---|---|
| Monoalkyl-substituted aromatic hydrocarbon (1) | 95–99 |
| Alkyl-substituted tetrahydronaphthalene (2) | 1–5 |

(1) Wherein the alkyl group is substantially linear and contains from 6 to 18 carbon atoms and wherein the aromatic moiety is phenyl, tolyl, xylyl, or ethylphenyl.
(2) Having approximately the same molecular weight as the monoalkyl-substituted aromatic hydrocarbon.

Suitable catalysts for use in the second alkylation step include aluminum chloride, aluminum bromide, and mixtures thereof. Aluminum chloride is preferred because of relative cost.

It is well known in the alkylation art that use of aluminum chloride or aluminum bromide as the catalyst requires the use of a hydrogen-donor promoter, such as water or hydrogen chloride. In many instances, sufficient water is present in situ in the materials used. The type and amount of promoter can be determined readily without undue experimentation by any person skilled in this art.

PROCESS CONDITIONS

First Alkylation Step

The first alkylation step, which uses hydrogen fluoride as the catalyst, is well known in the art and does not form the inventive feature of our process. However, in order to provide a more complete teaching of our invention, we will include a brief description of this alkylation step.

The relative amounts of linear olefin and aromatic hydrocarbon are as follows:

| Moles Olefin to Moles Aromatic Hydrocarbon | |
|---|---|
| Suitable | Preferred |
| 1:1–1:15 | 1:2–1:10 |

The amount of hydrogen fluoride is from about 1 to about 30 moles, preferably from about 1 to about 10 moles per mole of aromatic hydrocarbon.

The reaction is conducted at a temperature in the range of about 5° C. to about 100° C. The reaction time is in the range of 10 to 60 minutes.

Upon completion of the required reaction time, the reaction is terminated by separating the HF from the reaction mixture. The reaction mixture is then washed with NaOH solution, followed by removal of excess aromatic hydrocarbon by distillation.

Second Alkylation Step

The second step uses a long-chain alkylaromatic hydrocarbon, having been prepared using HF as the catalyst and linear olefin as the feedback. The relative amounts of olefin and long-chain alkylaromatic hydrocarbon are as follows:

| Moles Olefin/Moles Long-Chain Alkylaromatic Hydrocarbon | |
|---|---|
| Suitable | Preferred |
| 1:1–1:10 | 1:2–1:5 |

A desirable feature of our improved process is the use of severe reaction conditions in the second alkylation step. This can be accomplished by increasing the amount of catalyst or by use of higher temperatures; preferably, both features are used.

Expressed as amount of aluminum chloride or aluminum bromide per unit amount of olefin, a suitable amount of aluminum chloride or aluminum bromide is from about 2 to about 10 weight percent, preferably from about 3 to about 6 weight percent.

Suitably, the reaction is conducted using a temperature in the range of about 60 to about 90° C. Preferably, the reaction temperature is in the range of about 70 to about 80° C. A temperature as high as 100° C. can be used satisfactorily. Use of a lower temperature (e.g., to 50° C. is much less desirable because of the inferior low temperature physical properties of the product, particularly at comparable catalyst levels.

Knowing that the reaction is conducted under "severe conditions" and knowing the amounts of catalyst and the reaction temperature range, as described in the foregoing, any person skilled in this art can determine the required reaction time. Suitable reaction times are in the range of about 5 to about 360 minutes, preferably about 15 to about 90 minutes.

Upon completion of the required time of reaction, the reaction is terminated. The alkylation reaction product is introduced into a suitable separator where the catalyst sludge is removed. The catalyst-free alkylate product is then treated to remove residual acidic components and impurities. This can be readily accomplished by washing with water and/or a caustic solution or by percolating the alkylate through a bed of bauxite. Methods of purifying the crude alkylation reaction product are well known in the art.

After the alkylate reaction product has been treated in the manner described, it is then subjected to a fractional distillation in order to obtain the desired product, which is the bottom fraction.

The cut point for separating the desired bottoms fraction is determined by the molecular weight of the starting materials and by the physical properties desired in the bottoms fraction. In the preferred product, we have found cut points of about 165° C. to about 220° C. at 5 mm Hg can be used. In the most preferred product, a cut point of about 175°–190° C. at 5 mm Hg is used.

THE PRODUCT OF OUR INVENTION

The product of our invention consists essentially of di-long-chain alkyl aromatic hydrocarbons, wherein the alkyl and aromatic moieties are as defined in connection with the feedstock for the second (AlCl$_3$) alkylation step. To avoid any possible misunderstanding, the formula for the di-long-chain alkyl-substituted aromatic hydrocarbon, wherein the aromatic moiety is toluene, is as follows:

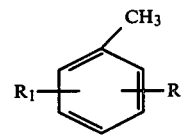

wherein R and R$_1$ are substantially linear alkyl groups containing about 6 to about 18 carbon atoms, preferably from about 10 to about 14 carbon atoms. As is implied, the term "long-chain" refers to those alkyl groups containing in the range of about 6 to about 18 carbon atoms. The product suitably contains above about 85 weight percent di-long-chain alkyl aromatic hydrocarbons. Preferably, the product contains above about 90 weight percent dialkylaromatic hydrocarbons.

The product may contain up to about 8 weight percent trialkyl-substituted tetrahydronaphthalenes. Other workers in this field have considered it desirable that the product contain 8 to 25, usually 10 to 15, weight percent trialkyl-substituted tetrahydronaphthalenes in order that the product have very good low temperature properties—particularly very good −40° F. viscosities. We have discovered that the product of our invention does not need trialkyl-substituted tetrahydronaphthalenes in order to have very good low temperature properties. It is our belief that our product has very good low temperature properties because of the structural nature of the dialkylaromatic hydrocarbon.

By way of background, and using phenyl as the aromatic moiety, alkylation of benzene with a linear mono-olefin produces an isomeric mixture of alkylbenzenes. Using a C$_{12}$ linear mono-olefin, the phenyl radical can be substituted on any carbon atom from the second to the eleventh. 2-phenyl dodecane can be shown as follows:

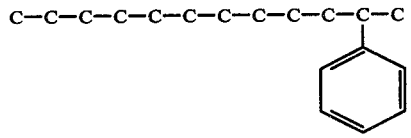

A 3-phenyl dodecane would have the phenyl radical on the third carbon atom.

Our process results in a product having a large amount of dialkylbenzenes (or aromatics) wherein one alkyl group has a high amount of "2-phenyl" substitution and the other alkyl group has a low amount of "2-phenyl" substitution. By high amount is meant above 20 weight percent, while low amounts mean less than 20 weight percent.

The product of our invention usually has a −40° F. viscosity of 15,000 cs or lower. Preferably, the −40° F. viscosity is 12,000 cs or lower. More preferably, the −40° F. viscosity does not exceed 10,000 cs. Accordingly, we can state the following limits for the $-40°$ F. viscosity of the product of our invention:

|  | Maximum Viscosity, cs |
| --- | --- |
| Suitable | 15,000 |
| Preferable | 12,000 |
| More Preferable | 10,000 |

The product of our invention also has the following physical properties:

|  | Suitable | Preferred |
| --- | --- | --- |
| Viscosity Index, at least | 100 | 110 |
| Pour Point, at least | $-50°$ F. | $-60°$ F. |

It is unexpected that the process forming our invention results in a product having low temperature viscosity properties, as described in the immediate foregoing. This is particularly the case when the product typically contains less than about 8 weight percent trialky-substituted tetrahydronaphthalenes.

In order to illustrate the nature of the present invention still more clearly, the following examples will be given. It is to be understood, however, that the invention is not to be limited to the specific conditions or details set forth in these examples except insofar as such limitations are specified in the appended claims.

EXAMPLE 1

This example illustrates the invention and shows the results obtained using HF in the first alkylation and AlCl$_3$ in the second alkylation. The procedure was as follows:

A. HF Alkylation

Benzene (8,000 grams) was added to a polyethylene reactor equipped with a stirrer, dropping funnel, and a vent. The benzene was cooled to 5°C. in an ice bath, and 4,000 grams of HF were condensed into the reactor. The admixture was stirred and held at 5° C. while 3,000 grams of 1-dodecene were added over a period of about one hour.

After the olefin addition was complete, the ice bath was removed and the HF allowed to evaporate overnight. When the reaction system was free of HF, the crude alkylate was washed with a 5 percent aqueous NaOH solution at about 90° C. allowed to settle, and the excess caustic solution removed. The crude alkylate was then distilled to remove benzene.

B. AlCl$_3$ Alkylation

Six moles of the monoalkylbenzene of step A were added to a creased flask equipped with stirrer, thermometer, condenser, and dropping funnel. To the flask was added a trace of HCl as a promoter and the AlCl$_3$ (5 weight percent based on the olefin used). One mole of 1-dodecane was then added in about one hour while the temperature was held at 50° C. After the olefin addition was completed, the admixture was stirred for an additional 30 minutes allowed to settle, and the sludge drawn off. The crude alkylate was washed with an aqueous 5 percent NaOh solution and then subjected to a distillation to remove unreacted monoalkylbenzene. The bottoms fraction was the desired product.

The properties of the product are shown in Table I.

EXAMPLE 2

This example is comparative and shows the results obtained using HF as the catalyst in both the first and second alkylation steps. The first alkylation step was the same as in Example 1. The second alkylation step was similar to the first alkylation step except that the monoalkylate of the first step was used in place of benzene. The amounts were equivalent on a molar basis. After washing, the crude alkylate was subjectd to distillation to recover the desired product as the bottom fraction.

The properties of the product are shown in Table I.

TABLE I

| | | PHYSICAL PROPERTIES | | | | |
| --- | --- | --- | --- | --- | --- | --- |
| Product | Meta/ Para | Pour Point, °F. | V.I. | Viscosities, cs | | |
| | | | | $-40°$ F. | 100° F. | 210° F. |
| Example 1 | 2.2 | $-75$ | 108 | 4,612 | 21.53 | 4.20 |
| Example 2 | 0.39 | $-75$ | 88 | 15,898 | 31.70 | 5.01 |

From the V.I.'s and $-40°$ F. viscosities, it is readily apparent that use of AlCl$_3$ in the second step gives a product having superior properties.

EXAMPLE 3

This example illustrates the invention and shows the results obtained using the process of Example 1 with a different feedstock in the second alkylation step. The feedstock was a mixed C$_{10}$–C$_{14}$ alkylbenzene which was prepared by alkylating benzene with a C$_{10}$–C$_{14}$ α-olefin mixture using HF as the catalyst. The monoalkylbenzene had the following homolog distribution:

|  | Wt. % |
| --- | --- |
| C-10 φ | 0.2 |
| C-11 φ | 1.0 |
| C-12 φ | 25.9 |
| C-13 φ | 32.4 |
| C-14 φ | 40.5 |

The product contained 3.0 weight percent alkyl-substituted tetrahydronaphthalenes in conjunction with the monoalkylbenzes.

The procedure used was the same as that in B of Example 1 except that mole ratios of 4:1 and 2:1, of monoalkylate to benzene, were used. Run "A" used a ratio of 4:1 while Run "B" used a ratio of 2:1. The trialkyl-substituted tetrahydronaphthalene content and the physical properties of the bottom product are shown in Table II.

TABLE II

| | | PHYSICAL PROPERTIES | | | | |
| --- | --- | --- | --- | --- | --- | --- |
| Run | % TTHN(1) | Pour Point, °F. | V.I. | Viscosities, cs | | |
| | | | | $-40°$ F. | 100° F. | 210° F. |
| A | 5.0 | $-70$ | 119 | 10,788 | 34.65 | 5.78 |
| B | <5.0 | $-65$ | 127 | 10,366 | 33.88 | 5.84 |

(1)trialkyl-substituted tetrahydronaphthalenes.

EXAMPLE 4

This example illustrates the effect of temperature variations and amount of AlCl$_3$ catalyst in the second alkylation step. The monoalkylate feedstock used was a C$_{14}$ monoalkylbenzene having a low "2-phenyl" isomer content. The run conditions and product properties are shown in Table III.

TABLE III

| Run No. | % AlCl₃ | Temp °C. | Meta/Para | Pour Point, °F. | V.I. | Viscosities, cs −40 °F. | 100° F. | 210° F. |
|---|---|---|---|---|---|---|---|---|
| A | 2 | 45 | 0.66 | −60 | 121 | 10,002 | 34.66 | 5.82 |
| B | 4 | 45 | 0.81 | −70 | 116 | 7,500 | 29.45 | 5.17 |
| C | 2 | 65 | 0.80 | −70 | 116 | 6,995 | 27.90 | 5.01 |
| D | 4 | 65 | 1.17 | −70 | 118 | 7,627 | 29.21 | 5.18 |

Inspection of Table III shows the following: (a) The products of Runs B, C, and D had superior physical properties to that of Run A, and (b) Runs B, C, and D were run under more severe reaction conditions than Run A.

Thus, having described the invention in detail, it will be understood by those skilled in the art that certain variations and modifications may be made without departing from the spirit and scope of the invention as defined herein and in the appended claims.

We claim:

1. A process for preparing a synthetic hydrocarbon lubricant composition, consisting essentially of di-long-chain alkyl aromatic hydrocarbons, wherein the long chain alkyl groups contain about 6 to about 18 carbon atoms and wherein the aryl moiety is phenyl, tolyl, xylyl, or ethylphenyl, said process comprising:
   (a) contacting from 1 to 15 moles of an aromatic hydrocarbon, which is benzene, toluene, xylene, or ethylbenzene, with 1 mole of a linear monoolefin containing about 6 to about 18 carbon atoms, in the presence of about 1 to about 30 moles hydrogen fluoride at a temperature in the range of about 5° C. to about 100° C.,
   (b) recovering from the reaction mass of step (a) mono-long-chain alkyl aromatic hydrocarbon, wherein the mono-long-chain is as defined,
   (c) contacting from 1 to 10 moles of the mono-long-chain alkyl aromatic hydrocarbon of step (b) with 1 mole of linear monoolefin containing about 6 to about 18 carbon atoms in the presence of from 2 to about 10 weight percent aluminum chloride or aluminum bromide, at a temperature of about 60 to about 90° C., and
   (d) recovering from the reaction mass of step (c) the di-long-chain alkyl aromatic hydrocarbon.

2. The process of claim 1 wherein step (a) is conducted using the following conditions:
   (a) moles of aromatic hydrocarbon to moles of olefin 2 to 10, and
   (b) moles of hydrogen fluoride to moles of aromatic hydrocarbon: 1 to 10.

3. The process of claim 2 wherein the amount of catalyst in step (c) is about 3 to about 6 weight percent, based on the olefin.

4. The process of claim 3 wherein the aromatic hydrocarbon is benzene.

5. The process of claim 4 wherein the product has a maximum viscosity at −40° F. of 12,000 centistokes.

6. The process of claim 5 wherein the product has a maximum viscosity at −40° F. of 10,000 centistokes.

7. A process for preparing a synthetic hydrocarbon lubricant composition, consisting essentially of di-alkylbenzenes, wherein the alkyl groups are linear and contain about 10 to about 14 carbon atoms, said process comprising:
   (a) contacting from 1 to 15 moles of benzene with 1 mole of a linear monoolefin containing about 10 to about 14 carbon atoms in the presence of about 1 to about 30 moles of hydrogen fluoride, at a temperature in the range of about 5° C. to about 100° C.,
   (b) recovering from the reaction mass of step (a) monoalkylbenzene wherein the alkyl group is linear and contains from about 10 to about 14 carbon atoms,
   (c) contacting from 1 to 10 moles of the monoalkylbenzene of step (b) with 1 mole of linear monoolefin containing from about 10 to about 14 carbon atoms in the presence of from 2 to 10 weight percent aluminum chloride or aluminum bromide, at a temperature of about 60 to about 90° C., and
   (d) recovering from the reaction mass of step (c) the di-$C_{10}$-$C_{14}$ alkylbenzene, said product having a viscosity at −40° F. of not more than 12,000 centistokes.

8. The process of claim 7 wherein step (a) is conducted using the following conditions:
   (a) moles of benzene to moles of olefin: 2 to 10, and
   (b) moles of hydrogen fluoride to moles of benzene: 1 to 10.

9. The process of claim 8 wherein the amount of catalyst in step (c) is about 3 to about 6 weight percent, based on the olefin.

10. The process of claim 9 wherein the product has a maximum viscosity at −40° F. of 10,000 centistokes.

* * * * *

UNITED STATES PATENT OFFICE
CERTIFICATE OF CORRECTION

PATENT NO. : 4,148,834  Page 1 of 2
DATED : April 10, 1979
INVENTOR(S) : Carl D. Kennedy and Gene E. Nicks It is certified that error appears in the above-identified patent and that said Letters Patent are hereby corrected as shown below:

Column 1, lines 26 and 27, after 3,173,965, "3,173,260" and "3,173,667" should be deleted.

Column 1, line 36, "Piror" should be --Prior--.

Column 1, line 37, "are" should be --art--.

Column 1, line 49, "Description" should be --Summary--.

Column 1, line 63, "fo" should be --of--.

Column 2, line 19, after olefins, "They can be either alpha or internal olefins." was omitted.

Column 3, line 13, "feedback" should be --feedstock--.

Column 3, line 61, "bottom" should be --bottoms--.

Column 5, line 60, "1-dodecane" should be --1-dodecene--.

Column 5, line 65, "NaOh" should be --NaOH--.

UNITED STATES PATENT OFFICE
CERTIFICATE OF CORRECTION

PATENT NO. : 4,148,834            Page 2 of 2

DATED : April 10, 1979

INVENTOR(S) : Carl D. Kennedy and Gene E. Nicks

It is certified that error appears in the above-identified patent and that said Letters Patent are hereby corrected as shown below:

Column 6, line 11, "bottom" should be --bottoms--.

Column 6, line 44, "monoalkylbenzes" should be --monoalkylbenzenes--.

Column 6, line 50, "bottom" should be --bottoms--.

Signed and Sealed this

Twenty-sixth Day of June 1979

[SEAL]

Attest:

RUTH C. MASON
Attesting Officer

DONALD W. BANNER
Commissioner of Patents and Trademarks